(12) United States Patent
Schäfer

(10) Patent No.: US 6,407,067 B1
(45) Date of Patent: Jun. 18, 2002

(54) SALTS OF THROMBIN INHIBITORS

(75) Inventor: Bernd Schäfer, Dierbach (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/559,047

(22) Filed: Apr. 27, 2000

(30) Foreign Application Priority Data

May 10, 1999 (DE) .......................... 199 21 345
Oct. 1, 1999 (DE) .......................... 199 47 479

(51) Int. Cl.[7] .......................... A61F 2/06; A61F 2/24; A61K 38/05; A61L 33/12; A61M 1/14
(52) U.S. Cl. .................... 514/19; 210/500.24; 210/646; 422/45; 514/970; 514/973; 623/1.43; 623/1.46; 623/2.42
(58) Field of Search .................. 514/19, 769, 788, 514/970, 973; 544/2, 266, 267, 285, 309; 548/211, 213, 480, 545, 548; 562/37, 104; 210/646, 647, 500, 24; 422/44, 45, 46, 47, 48; 604/4.01, 5.01, 5.04, 6.07, 6.14; 623/1.42, 1.43, 1.46, 2.42

(56) References Cited

U.S. PATENT DOCUMENTS 5,055,461 A * 10/1991 Kelleher et al. ............ 514/162
6,030,972 A    2/2000 Böhm et al. .................. 514/257

FOREIGN PATENT DOCUMENTS

| WO | WO 94/29336 | 12/1994 |
| WO | WO 96/25426 | 8/1996 |
| WO | WO 98/09950 | 3/1998 |

OTHER PUBLICATIONS

Grant, J., ed. Hackh's Chemical Dictionary, 4th ed. New York: McGraw–Hill Book Co. p. 95, 1969.*

Houben–Weyl, band I/1, Georg Tehima Verlag, Stuttgart, 1958 pp. 341–390.

Römpps Chemie–Lexikon, 8. Ed., Franckh'sche Verlagshandlung, Stuttgart, 1983, S 2244–2246.

* cited by examiner

Primary Examiner—Jeffrey E. Russel
(74) Attorney, Agent, or Firm—Keil & Weinkauf

(57) ABSTRACT

Compounds having thrombin inhibiting activity of the general formula I or II

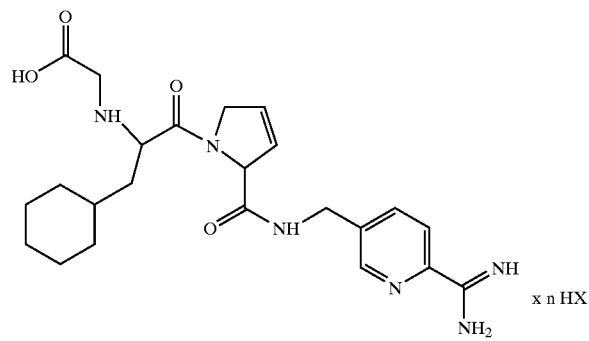

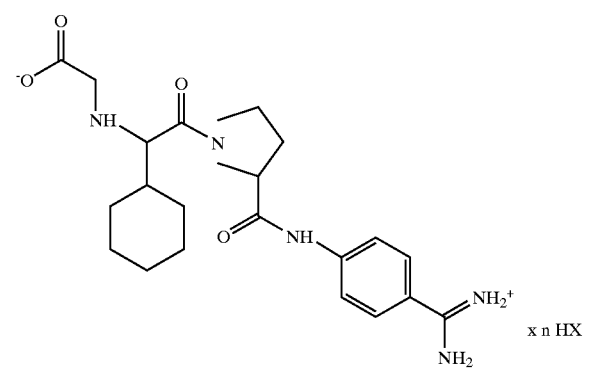

where n is 0.5, 1, 2 and HX is

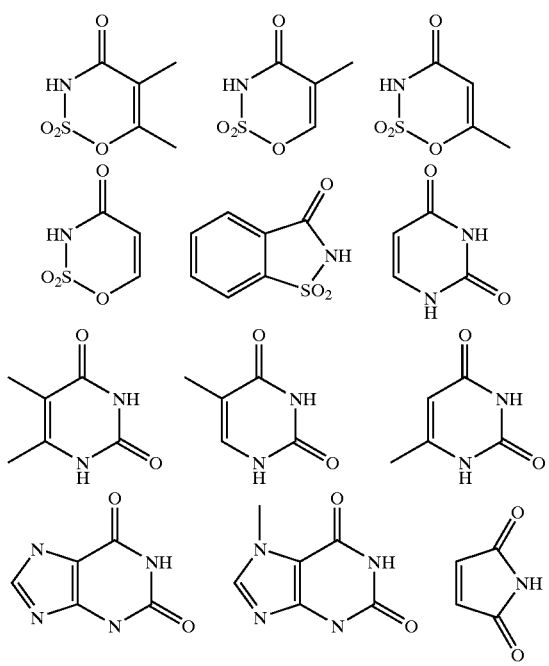

-continued
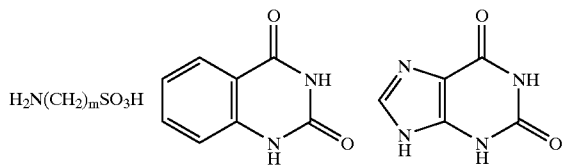
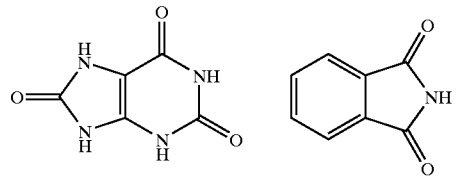
-continued
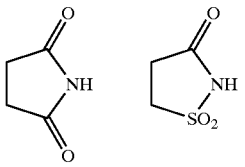
and HX is optionally substituted once or twice by methyl, ethyl or hydroxyl, and the tautomers and stereoisomers thereof, which compounds have greater thermal stability betaines, and salts of mineral acids or $C_1$–$C_4$-carboxylic acids.
10 Claims, No Drawings

SALTS OF THROMBIN INHIBITORS

The invention relates to novel salts of thrombin inhibitors, their preparation and use for producing drugs with antithrombotic effect.

The invention specifically relates to novel compounds of the general formula I or II

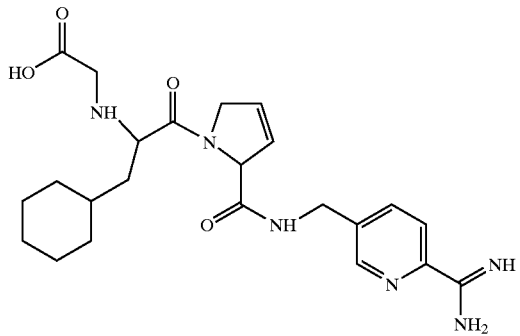

(I)

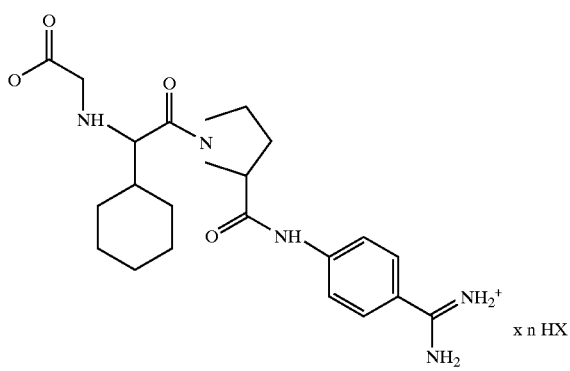

(II)

where n is 0.5, 1, 2 and

HX is

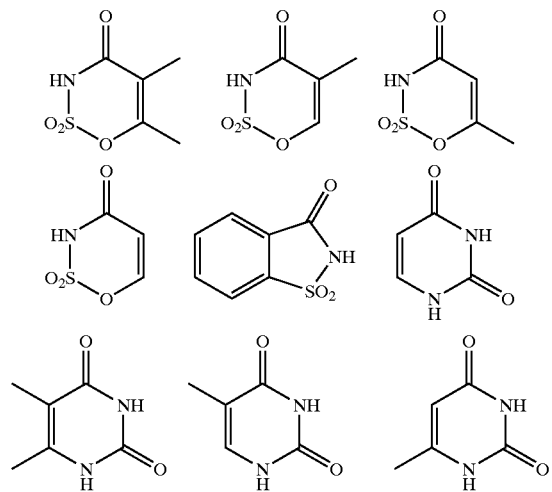

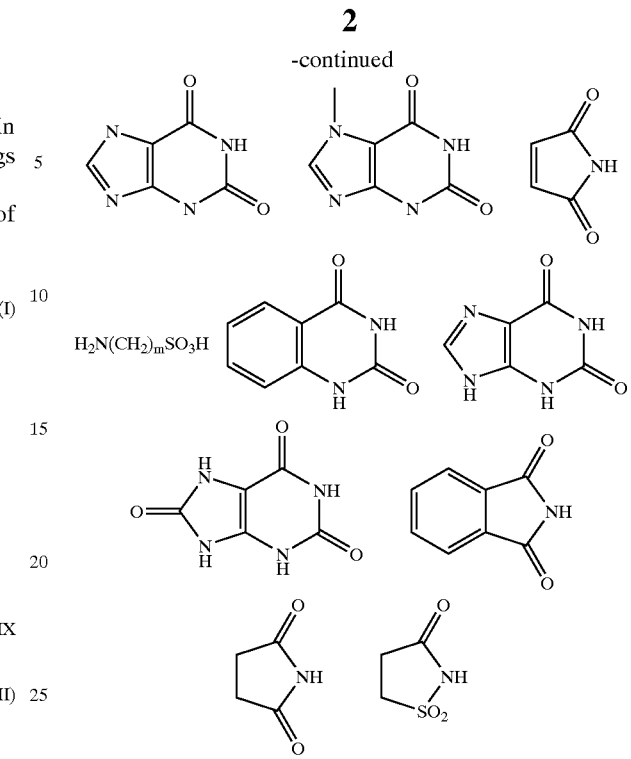

and HX is optionally substituted once or twice by methyl, ethyl or hydroxyl, and the tautomers and stereoisomers thereof, and m is from 0 to 4.

The preferred meanings of HX are as follows:

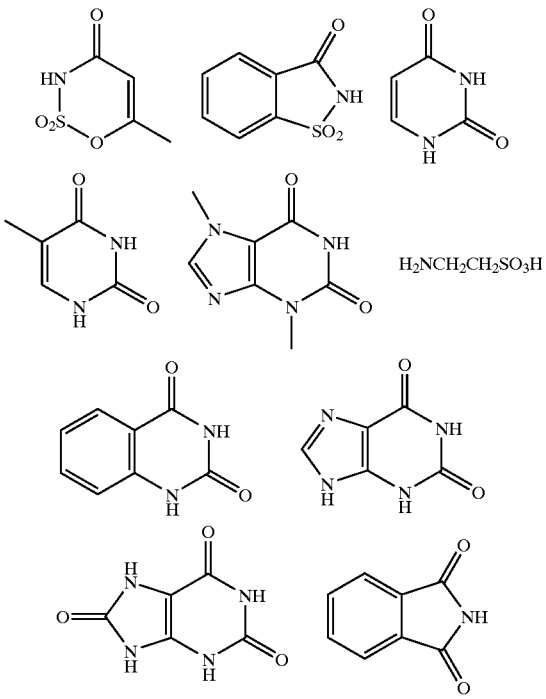

The particularly preferred active substance of the formula I has the R configuration of cyclohexylalanine and the S configuration of dehydroproline.

The preparation of the thrombin inhibitor I with HX=HOAc is described in WO 96/25426, and that of the thrombin inhibitor II with n=0 is described in WO 94/29336.

The salts are usually amorphous. Storage of these products, especially at elevated temperature, leads to the formation of a number of byproducts.

It is an object of the present invention to find storage-stable forms of the active substances.

The betaines of the active substances are obtained by titrating the acidic salts to the isoelectric point, precipitation or crystallization, filtration or centrifugation and drying. The salts of the general formula I and II are obtained by reacting the betaines with HX, or else the alkali metal salt of HX is reacted with the mineral acid salts or $C_1$–$C_4$-carboxylic acid salts of I or II. Suitable solvents are water, $C_1$–$C_6$-alcohols, $C_1$–$C_6$-ethers, $C_1$–$C_6$-esters, toluene, xylenes, DMF, DMSO, THF. Water is the very preferred solvent. The product is isolated by filtration or centrifugation and drying or from a solution by freeze drying or spray drying.

All conventional methods are suitable for producing crystals, as described, for example, in Houben-Weyl, volume I/1, Georg Thieme Verlag, Stuttgart, 1958, 341; R ömpps Chemie-Lexikon, 8th edition, Franckh'sche Verlagshandlung, Stuttgart, 1983, 2244, and the literature quoted therein.

The usual physiologically tolerated salts of I and II are normally amorphous solids. We have now found, surprisingly, that, in particular, the salts with acesulfame-K and saccharin are compounds which crystallize well. They precipitate spontaneously from water. However, addition of minimal amounts of water in the range from 5 to 500% by weight to a solid, stoichiometric mixture of I or II with HX also suffices to obtain crystalline substances.

The salt formation is normally carried out batchwise in reaction vessels. However, continuous production, for example in a cascade of stirred vessels or in an extruder, is also possible. The process is so robust that it can also be carried out by mixing solids in an apparatus suitable for this purpose, preferably in one used for formulating pharmaceutical active substances.

The crystallization temperature is generally in the range from −80 to 200° C., preferably in the range from −20 to 150° C.

The pressure is in the range from 1 bar to 2000 bar.

The crystallinity of the samples has been assessed on the basis of Debye-Scherrer photographs.

The thermal decomposition of the compounds of the general formula I and II has been investigated in a stability test. This was done by storing the compounds I or II in an atmospheric pressure at 70° C. for 10 days and determining the relative decrease in the content by HPLC analysis at an interval of 7 days in each case.

We have now found, surprisingly, that the salts of the general formula I and II are considerably more stable than the betaine and salts of mineral acids and $C_1$–$C_4$-carboxylic acids. The crystallinity of the salts is particularly advantageous for the stability of the active substance.

The novel salts of the general formula I or II can be employed for the following indications:

diseases whose pathomechanism is based directly or indirectly on the proteolytic effect of thrombin, diseases whose pathomechanism is based on thrombin-dependent activation of receptors and signal transduction, diseases associated with stimulation (for example by PAI-1, PDGF (plated derived growth factor), P-selectin, ICAM-1, tissue factor or inhibition (for example NO synthesis in smooth muscle cells) of the expression of genes in body cells, diseases based on the mitogenic effect of thrombin, diseases based on a thrombin-dependent change in contractility and permeability of epithelial cells (for example vascular endothelial cells), thrombin-dependent thromboembolic events such as deep vein thrombosis, pulmonary embolism, myocardial or cerebral infarct, atrial fibrillation, bypass occlusion, disseminated intravascular coagulation (DIC), reocclusion and for reducing the reperfusion time on comedication with thrombolytics such as streptokinase, urokinase, prourokinase, t-PA, APSAC, plasminogen activators from the salivary glands of animals, and the recombinant and mutated forms of all these substances, the occurrence of early reocclusion and late restenosis after PTCA, thrombin-dependent proliferation of smooth muscle cells, accumulation of active thrombin in the CNS (for example in Alzheimer's disease), tumor growth, and to prevent adhesion and metastasis of tumor cells.

The novel compounds can be employed in particular for the therapy and prophylaxis of thrombin-dependent thromboembolic events such as deep vein thromboses, pulmonary embolisms, myocardial or cerebral infarcts and unstable angina, also for the therapy of disseminated intravascular coagulation (DIC). They are also suitable for combination therapy with thrombolytics such as streptokinase, urokinase, prourokinase, t-PA, APSAC and other plasminogen activators to reduce the reperfusion time and extend the reocclusion time.

Further preferred areas of use are the prevention of thrombin-dependent early reocclusion and late restenosis after percutaneous transluminal coronary angioplasty, the prevention of thrombin-induced proliferation of smooth muscle cells, the prevention of the accumulation of active thrombin in the CNS (for example in Alzheimer's disease), the control of tumors and the prevention of mechanisms which lead to the adhesion and metastasis of tumor cells.

The novel compounds can also be used for coating artificial surfaces such as hemodialysis membranes and the tubing systems and lines necessary therefor, and oxygenators of an extravascular circulation, stents and heart valves.

The novel compounds can also be employed for diseases whose pathomechanism is based directly or indirectly on the proteolytic effect of kininogenases, in particular kallikrein, for example for inflammatory diseases such as asthma, pancreatitis, rhinitis, arthritis, urticaria and other internal inflammatory diseases.

The compounds according to the invention can be administered orally or parenterally (subcutaneously, intravenously, intramuscularly, intraperitoneally, rectally) in a conventional way. Administration can also take place with vapors or sprays through the nasopharyngeal space. The compounds can, in particular, be given orally.

The dosage depends on the age, condition and weight of the patient and on the mode of administration. The daily dose of active substance per person is usually between about 10 and 2000 mg on oral administration and between about 1 and 200 mg on parenteral administration. This dose can be given in 2 to 4 single doses or once a day as depot form.

The novel compounds can be used in conventional solid or liquid pharmaceutical forms, for example as uncoated or (film-)coated tablets, capsules, powders, granules, suppositories, solutions, ointments, creams or sprays. These are produced in a conventional way. The active substances can for this purpose be processed with conventional pharmaceutical excipients such as tablet binders, bulking agents, preservatives, tablet disintegrants, flow regulators, plasticizers, wetting agents, dispersants, emulsifiers, solvents, release-slowing agents, antioxidants and/or propellant gases (cf. H. Sucker et al.: Pharmazeutische Technologie, Thieme-Verlag, Stuttgart, 1978). The administration forms obtained in this way normally contain the active substance in an amount of from 0.1 to 99% by weight.

COMPARATIVE EXAMPLES

1st Example

N-((Hydroxycarbonyl)methylene)-(R)-cyclohexylalanyl-(S)-3,4-dehydroproline 6-Amidino-3-picolinylamide (Betaine)

90 g (0.116 mol) of the compound N-Boc-N-((t-butoxycarbonyl)methylene)-(R)-cyclohexylalanyl-(S)-3,4-dehydroproline 6-amidino-3-picolinylamide N-acetyl-(S)-cysteinate which is described in Example 3 of WO 98/09950, 360 g of water and 44.56 g (38% strength, 0.464 mol) of hydrochloric acid were heated at 65° C. for 2 h. After cooling to room temperature and extraction once with ethyl acetate, the phases were separated and adjusted to pH 8.2 with 105 g of a 25% strength aqueous ammonia solution. The product then precipitated. Stirring for one hour was followed by filtration with suction, washing with ice-water and then drying in a vacuum oven. 41.66 g (0.091 mol, 79%) of N-((hydroxycarbonyl)methylene)-(R)-cyclohexylalanyl-(S)-3,4-dehydroproline 6-amidino-3-picolinylamide were obtained in the form of a colorless solid. Debye-Scherrer photograph: amorphous

2nd Example

N-((hydroxycarbonyl)methylene)-(R)-cyclohexylalanyl-(S)-3,4-dehydroproline 6-Amidino-3-picolinylamide Fumarate 3 g (6.6 mmol) of N-((hydroxycarbonyl)methylene)-(R)-cyclohexylalanyl-(S)-3,4-dehydroproline 6-amidino-3-picolinylamide were introduced into 30 ml of water, and 0.686 g (6 mmol) of fumaric acid was added. The reaction mixture was stirred at room temperature overnight and then freeze dried. 3.2 g (5.6 mmol, 93%) of N-((hydroxycarbonyl)methylene)-(R)-cyclohexylalanyl-(S)-3,4-dehydroproline 6-amidino-3-picolinylamide fumarate were obtained in the form of a colorless powder Debye-Scherrer photograph: amorphous

3rd Example

N-((Hydroxycarbonyl)methylene)-(R)-cyclohexylalanyl-(S)-3,4-d ehydroproline 6-Amidino-3-picolinylamide Acetate 3 g (6.6 mmol) of N-((hydroxycarbonyl)methylene)-(R)-cyclohexylalanyl-(S)-3,4-dehydroproline 6-amidino-3-picolinylamide were introduced into 30 ml of water, and 0.39 g (6.5 mmol) of acetic acid was added. The reaction mixture was stirred at room temperature overnight and then freeze dried. 3.4 g (6.5 mmol, 100%) of N-((hydroxycarbonyl)methylene)-(R)-cyclohexylalanyl-(S)-3,4-dehydroproline 6-amidino-3-picolinylamide acetate were obtained in the form of a colorless powder Debye-Scherrer photograph: amorphous

Examples

4th Example

N-((Hydroxycarbonyl)methylene)-(R)-cyclohexylalanyl-(S)-3,4-dehydroproline 6-Amidino-3-picolinylamide Acesulfamate 3.5 g (6.6 mmol) of N-((hydroxycarbonyl)methylene)-(R)-cyclohexylalanyl-(S)-3,4-dehydroproline 6-amidino-3-picolinylamide hydrochloride in 15 ml of water and 1.33 g (6.6 mmol) of acesulfame-K in 15 ml of water were mixed. The product started to crystallize after about 2.5 hours. After stirring overnight, the product was filtered off, washed once with 5 ml of water and dried in an oven at 70° C. 1.4 g (2.4 mmol, 37%) of N-((hydroxycarbonyl)methylene)-(R)-cyclohexylalanyl-(S)-3,4-dehydroproline 6-amidino-3-picolinylamide acesulfamate were obtained in the form of a colorless powder.

Debye-Scherrer photograph: crystalline

5th Example

N-( (Hydroxycarbonyl)methylene)-(R)-cyclohexylalanyl-(s)-3,4-dehydroproline 6-Amidino-3-picolinylamide Saccharinate 3 g (6.6 mmol) of N-((hydroxycarbonyl)methylene)-(R)-cyclohexylalanyl-(S)-3,4-dehydroproline 6-amidino-3-picolinylamide were introduced into 30 ml of water, and 1.2 g (6.6 mol) of saccharin were added. After 1.5 h, the product was filtered off with suction, washed with water and dried in a vacuum oven. 2.5 g (3.9 mmol, 59%) of N-((hydroxycarbonyl)-methylene)-(R)-cyclohexylalanyl-(S)-3,4-dehydroproline 6-amidino-3-picolinylamide saccharinate were obtained in the form of a colorless powder.

Debye-Scherrer photograph: crystalline

6th Example

N-((Hydroxycarbonyl)methylene)-(R)-cyclohexylalanyl-(S)-3,4-dehydroproline 6-Amidino-3-picolinylamide Saccharinate 2.9 g (12 mmol) of saccharin sodium salt were dissolved in 10 ml of water, and 6.36 g (93% pure, 12 mmol) of N-((hydroxycarbonyl)-methylene)-(R)-cyclohexylalanyl-(S)-3,4-dehydroproline 6-amidino-3-picolinylamide hydrochloride dissolved in 30 ml of water were slowly added dropwise. The mixture was left to stir for 4 h, and the product was filtered off with suction, washed with water and dried in a vacuum oven. 6 g (9.4 mmol, 78%) of N-((hydroxy-carbonyl)methylene)-(R)-cyclohexylalanyl-(S)-3,4-dehydroproline 6-amidino-3-picolinylamide saccharinate were obtained in the form of a colorless powder.

Debye-Scherrer photograph: crystalline

7th Example

Stability Test

The substances were stored at 70° C., 1 bar. Measurements were in HPLC % areas

TABLE 1

Stability of salts of the compound I on storage in an open vessel

| Days | Acesulfame salt n = 1 | Saccharin salt n = 1 | Acetate n = 1 | Fumarate n = 1 |
|---|---|---|---|---|
| 0 | 100 | 100 | 100 | 100 |
| 7 | 96,7 | 100 | 92.6 | 87.9 |
| 14 | 88,4 | 101 | 87.2 | 87.1 |

TABLE 2

Stability of the compound II on storage in a closed vessel

| Days | HCl salt | Saccharin salt |
|---|---|---|
| 0 | 100 | 100 |
| 7 | 99.3 | 100 |
| 14 | 98.9 | 100 |

I claim:

1. A compound of the formula I or II

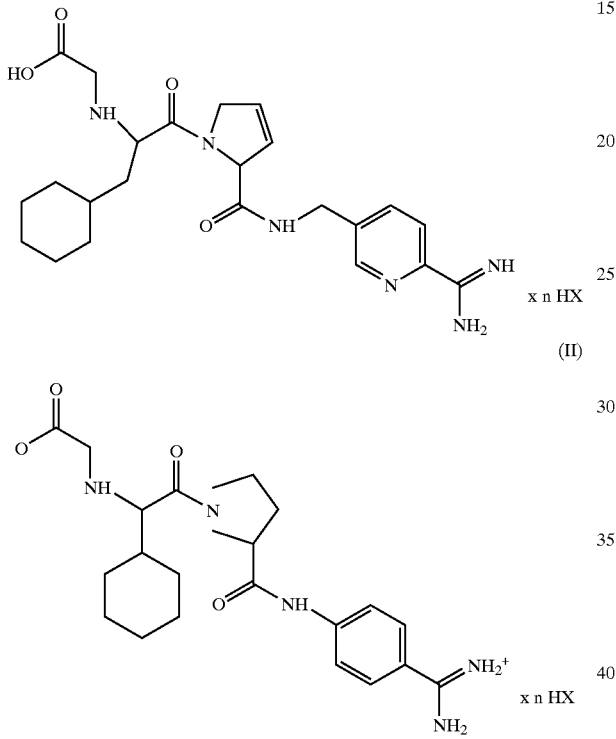

where n is 0.5, 1, 2 and

HX is

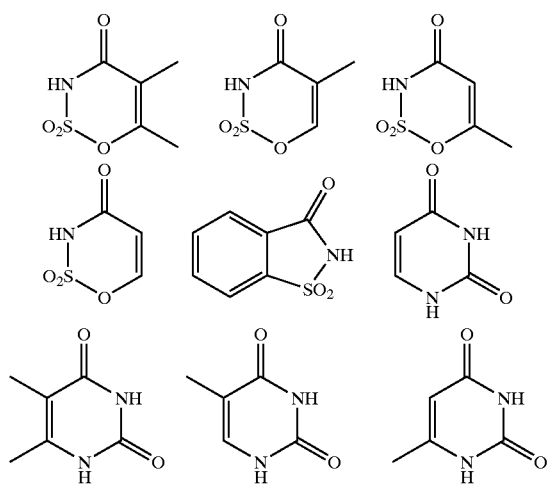

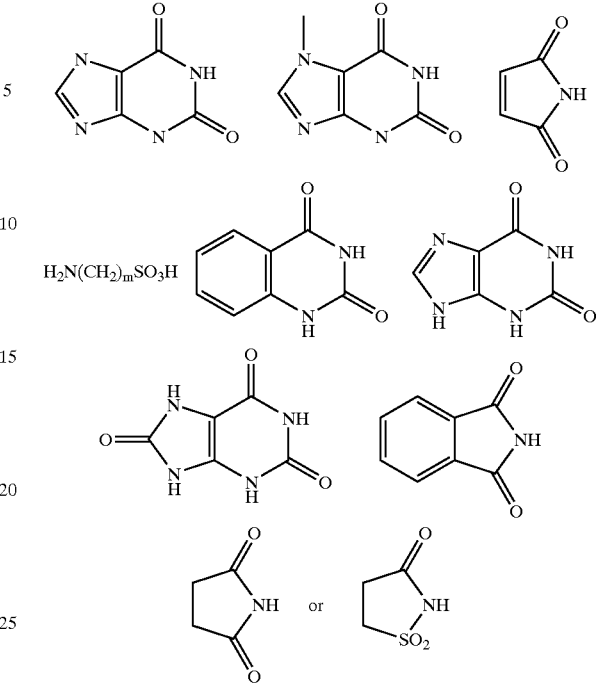

and HX is optionally substituted once or twice by methyl, ethyl or hydroxyl, and the tautomers and stereoisomers thereof, and m=0 to 4.

2. A compound as claimed in claim 1 in crystalline form.

3. A process for preparing a compound of the formula I as claimed in claim 1, where the betaine of I or II (n=0) is reacted with n HX.

4. A process for preparing a compound of the formula I as claimed in claim 1, where a mineral acid salt or $C_1$–$C_4$-carboxylic acid salt of the compound of the formula I or II is reacted with an alkali metal salt of HX.

5. A process as claimed in claim 3, wherein the compound of the formula I or II is prepared in water.

6. A process as claimed in claim 4, wherein the compound of the formula I or II is prepared in water.

7. A process as claimed in claim 6, wherein a solid stoichiometric mixture of a mineral acid salt or $C_1$–$C_4$-carboxylic acid salt of a compound of the formula I or II is caused to react with an alkali metal salt of HX in from 5 to 500% by weight of water.

8. A drug comprising as the pharmaceutically active substance a compound of the formula I or II as claimed in claim 1 in addition to carriers and excipients.

9. A method of treating
   diseases whose pathomechanism is based directly or indirectly on the proteolytic effect of thrombin,
   diseases whose pathomechanism is based on the thrombin-dependent activation of receptors and signal transduction,
   diseases associated with stimulation or inhibition of the expression of genes in body cells,
   diseases based on the mitogenic effect of thrombin,
   diseases based on a thrombin-dependent change in contractility and permeability of epithelial cells,
   thrombin-dependent thromboembolic events,
   disseminated intravascular coagulation,
   reocclusion and for reducing the reperfusion time on comedication with thrombolytics, the occurrence of early reocclusion and late restenosis after PTCA, thrombin-dependent proliferation of smooth muscle cells, accumulation of active thrombin in the CNS, or tumor growth, and to prevent adhesion and metastasis of tumor cells, in a mammal in need of such treatment, comprising administering to said mammal an effective amount of a compound of formula I or II as claimed in claim 1.

10. A hemodialysis membrane, tubing system or line, an extrovascular oxygenator, a stent or a heart valve coated with a compound of formula I or II as claimed in claim 1.

* * * * *